US010010600B2

(12) United States Patent
Stinchcomb et al.

(10) Patent No.: US 10,010,600 B2
(45) Date of Patent: *Jul. 3, 2018

(54) COMPOSITIONS AND METHODS FOR ADMINISTRATION OF VACCINES AGAINST DENGUE VIRUS

(71) Applicant: Takeda Vaccines, Inc., Deerfield, IL (US)

(72) Inventors: Dan T. Stinchcomb, Fort Collins, CO (US); Jorge E. Osorio, Mount Horeb, WI (US); Charalambos D. Partidos, Chicago, IL (US); Joseph N. Brewoo, Madison, WI (US)

(73) Assignee: TAKEDA VACCINES, INC., Cambridge, MD (US)

( * ) Notice: Subject to any disclaimer, the term of this patent is extended or adjusted under 35 U.S.C. 154(b) by 50 days.

This patent is subject to a terminal disclaimer.

(21) Appl. No.: 14/935,281

(22) Filed: Nov. 6, 2015

(65) Prior Publication Data

US 2016/0129102 A1    May 12, 2016

Related U.S. Application Data

(63) Continuation of application No. 12/790,511, filed on May 28, 2010, now Pat. No. 9,211,323.

(60) Provisional application No. 61/183,020, filed on Jun. 1, 2009.

(51) Int. Cl.
  *A61K 39/12* (2006.01)
  *A61K 9/00* (2006.01)
  *A61K 39/00* (2006.01)

(52) U.S. Cl.
  CPC .......... *A61K 39/12* (2013.01); *A61K 9/0019* (2013.01); *A61K 2039/5254* (2013.01); *A61K 2039/54* (2013.01); *A61K 2039/545* (2013.01); *A61K 2039/70* (2013.01); *C12N 2770/24134* (2013.01)

(58) Field of Classification Search
  None
  See application file for complete search history.

(56) References Cited

U.S. PATENT DOCUMENTS

| | | | |
|---|---|---|---|
| 7,094,411 B2 | 8/2006 | Kinney et al. | |
| 7,641,908 B2 | 1/2010 | Kinney et al. | |
| 7,718,358 B2 | 5/2010 | Guy et al. | |
| 8,968,996 B2 | 3/2015 | Stinchcomb | |
| 9,211,323 B2 | 12/2015 | Stinchcomb et al. | |
| 9,713,638 B2 | 7/2017 | Stinchcomb et al. | |
| 2004/0120964 A1 | 6/2004 | Mikszta et al. | |
| 2004/0259224 A1 | 12/2004 | Guirakhoo | |
| 2006/0062803 A1* | 3/2006 | Kinney | A61K 39/295 424/199.1 |
| 2006/0246081 A1 | 11/2006 | Deem et al. | |
| 2007/0026016 A1 | 2/2007 | Kinney et al. | |
| 2007/0269458 A1 | 11/2007 | Guirakhoo et al. | |
| 2008/0085288 A1 | 4/2008 | Guy et al. | |
| 2008/0193477 A1 | 8/2008 | Monath et al. | |
| 2010/0158938 A1 | 6/2010 | Guirakhoo | |
| 2010/0303860 A1* | 12/2010 | Stinchcomb | A61K 39/12 424/218.1 |
| 2012/0093864 A1 | 4/2012 | Deem et al. | |
| 2015/0150961 A1 | 6/2015 | Stinchcomb et al. | |

FOREIGN PATENT DOCUMENTS

| | | |
|---|---|---|
| JP | 2003523189 A | 8/2001 |
| JP | 2002325593 A | 11/2002 |
| JP | 2002540168 A | 11/2002 |
| JP | 2005507898 | 3/2005 |
| JP | 2009504654 A | 2/2009 |
| JP | 2010505801 A | 2/2010 |
| WO | 2001060847 A2 | 8/2001 |
| WO | 2000057907 A9 | 4/2002 |
| WO | WO02095075 A1 | 11/2002 |
| WO | 2007021672 A2 | 2/2007 |
| WO | 2008022196 A2 | 2/2008 |
| WO | 2008047023 A2 | 4/2008 |
| WO | 2008063995 A9 | 9/2008 |
| WO | 2008157136 A1 | 12/2008 |
| WO | 2010141386 A1 | 12/2010 |

OTHER PUBLICATIONS

International Search Report and Written Opinion issued in PCT/US10/36726, dated Jul. 28, 2010, 8 pages.
Apt et al. Tetravalent Neutralizing Antibody Response Against Four Dengue Serotypes by a Single Chimeric Dengue Envelope Antigen; Vaccine vol. 24, Issue 3, Jan. 16, 2006, pp. 335-344.
Blaney, Joseph E. Jr. et al., Recombinant, Live-Attenuated Tetravalent Dengue Virus Vaccine Formulations Induce a Balanced, Broad, and Protective Neutralizing Antibody Response against Each of the Four Serotypes in Rhesus Monkeys, Journal of Virology, vol. 79, No. 9, (May 2005) pp. 5516-5528.
Brewoo, Joseph N. et al., Immunogenicity and efficacy of chimeric dengue vaccine (DENVax) formulations in interferon-deficient AG129 mice, ScienceDirect, (Nov. 19, 2011).
Cannon, D.A. et al., Mass vaccination against yellow fever by scarification with 17d strain vaccine, Federal Laboratory Service, Yaba, Lagos, Nigeria, Apr. 30, 1957, pp. 256-263.

(Continued)

*Primary Examiner* — Stacy Brown Chen
(74) *Attorney, Agent, or Firm* — Faegre Baker Daniels LLP (57) ABSTRACT

Embodiments of the present invention report compositions and methods for vaccinating a subject against dengue viruses. In some embodiments, vaccine compositions may be administered by intradermal introduction. In certain embodiments, intradermal introduction in a subject of a vaccine against dengue virus may include one or more intradermal boosts after initial vaccination. Other embodiments include intradermal injection of a vaccine composition against dengue virus wherein the composition provides protection against two or more of DEN-1, DEN-2, DEN-3 and DEN-4.

15 Claims, 4 Drawing Sheets

(56) References Cited

OTHER PUBLICATIONS

Osorio, Jorge E. et al., Efficacy of a Tetravalent Chimeric Dengue Vaccine (DENVax) in Cynomolgus Macaques, Am.J. Trop.Med. Hyg., vol. 84, No. 6, (2011) pp. 978-987.
Webster et al., Lancet Infectious Disease, 2009, 9:678-687.
Zhou, H., et al. Sculpting the Immunological Response to Dengue Fever by Polytopic Vaccination. Vaccine, 24(14): 2451-2459, Mar. 24, 2006.
Zompi and Harris, Viruses, 2012, 4:62-82.
Cannon, D.A. et al., Vaccination by scarification with 17d yellow fever vaccine prepared at YABA, Lagos, Nigeria, Laboratory Service Headquarters, Yaba, Lagos, Nigeria, Oct. 8, 1953, pp. 380-393.
Capeding, Rosario Z. et al., Live-attenuated, tetravalent dengue vaccine in children, adolescents and adults in a dengue endemic country: Randomized controlled phase I trial in the Philippines, Elsevier, Vaccine, vol. 29, (2011) pp. 3863-3872.
Dean, Cheryl H. et al., Cutaneous Delivery of a Live, Attenuated Chimeric Flavivirus Vaccine Against Japanese Encephalitis, Human Vaccines, vol. 1, No. 3, (2005) pp. 106-111.
Guy, Bruno et al., Evaluation of Interferences between Dengue Vaccine Serotypes in a Monkey Model, Am.J.Trop. Med.Hyg., vol. 80, No. 2, (2009) pp. 302-311.
Higgs, et al., Growth Characteristics of Chimerivax-Den Vaccine Viruses in Aedes Aegypti and Aedes Albopictus From Thailand, Am. J. Trap. Med. Hyg., 75(5), (2006), pp. 986-993.
Huang C Y-H et al: "Dengue 2 PDK-53 virus as a chimeric carrier for tetravalent dengue vaccine development" Journal of Virology. The American Society for Microbiology. US. vol. 77. No. 21. Nov. 1, 2003 (Nov. 1, 2003). pp. 11436-11447. XP003005064. ISSN: 0022-538X. DOI: 10.1128/JVI.77.21.11436-11447.2003 p. 11436—col. 2; table 1.
International Preliminary Report on Patentability issued in PCT/US2013/045041, dated Dec. 16, 2014, 6 pages.
Inviragen, Dengue, Feb. 13, 2013, found at http://www.inviragen.com/dengue.php.
Meers, Captain P.D., Further Observations on 17D-Yellow Fever Vaccination by Scarification, With and Without Simultaneous Smallpox Vaccination, Transactions of the Royal Society of Tropical Medicine and Hygiene, vol. 54, No. 5, (1960) pp. 493-501.
Osorio, Jorge E. et al., Development of DENVax: A chimeric dengue-2 PDK-53-based tetravalent vaccine for protection against dengue fever, ScienceDirect, vol. 29, (2011) pp. 7251-7260.
Osorio, Jorge E. et al., Development of DENVax: A chimeric dengue-2 PDK-53-based tetravalent vaccine for protection against dengue fever, Vaccine, vol. 29, (2011) pp. 7251-7260.
Gubler, Duane J. "Dengue and Dengue Hemorrhagic Fever." Clinical Microbiology Reviews, 11(3):480-496, Jul. 1998.
Halstead, Scott B., et al. Studies on the Immunization of Monkeys Against Dengue: II. Protection Following Inoculation of Combinations of Viruses. The American Journal of Tropical Medicine and Hygiene, 22(3):375-381, (1973).
O'Hagan, Derek T., et al. Novel Approaches to Pediatric Vaccine Delivery. Advanced Drug Delivery Reviews 58:29-51, 2006.
Rothman, Alan L., et al. "Induction of T Lymphocyte Responses to Dengue Virus by a Candidate Tetravalent Live Attenuated Dengue Virus Vaccine." Vaccine, 19:4694-4699, 2001.
Schmidt, Alexander. "Presentation Abstract: Tetravalent Dengue Purified Inactivated Vaccine (DPIV): status of the GSK/FIOCRUZ/U.S. Army Dengue Vaccine Candidate," presented at the Cooperation Among First-to-Introduce Countries for Dengue Vaccines 2013 Meeting, hosted by the Ministry of Health of Brazil in Brasilia, Abstract, 1 page.
Schmidt, Alexander. "Tetravalent dengue purified inactivated vaccine (DPIV): status of the GSK/FIOCRUZ/US Army dengue vaccine candidate." [Online] Blog Series: NIAID-DVI, Sep. 29, 2013, 2 pages, [retrieved Aug. 18, 2016]. Retrieved from the Internet: <http://weallseqtoseq.blogspot.com/2013/09/niaid-dvi-gskfiocruzus-tetravalent-dpiv.html>.
Sabin, Albert B. Research on Dengue During World War II. The American Journal of Tropical Medicine and Hygiene 1, pp. 30-50, 1952.
Bhamarapravati, N., et al. "Live Attenuated Tetravalent Dengue Vaccine." Vaccine, 18:44-47, 2000.
Bhamarapravati, Natth, et al. "The Clinical Trial of Trivalent Dengue Vaccine." Southeast Asian Journal of Tropical Medicine and Public Health, 1990, 21(4), [Abstract], p. 709, 1990.
Clinical Microbiology, 2002, vol. 2 p. 25-29 (Japanese Article with English translation of abstract).
Halstead, Scott B., et al. "Studies the Immunization of Monkeys Against Dengue." The American Journal of Tropical Medicine Hygiene, 22(3):365-374, 1973.
Kochel et al. A Dengue Virus Serotype-1 DNA Vaccine Induces Virus Neutralizing Antibodies and Provides Protection From Viral Challenge in Aotus Monkeys, Vaccine, vol. 18, No. 18, Jul. 1, 2000, pp. 3166-3173.

\* cited by examiner

Fig. 1

Pharmajet®

Fig. 2

Fig. 3 Immune Response after Primary Immunization

Fig. 4 Immune Response after Boost

COMPOSITIONS AND METHODS FOR ADMINISTRATION OF VACCINES AGAINST DENGUE VIRUS

PRIORITY

This application is a U.S. divisional application that claims priority to U.S. Non-provisional patent application Ser. No. 12/790,511 filed May 28, 2010, now U.S. Pat. No. 9,211,323, issued Dec. 15, 2015; which claims the benefit of U.S. Provisional Patent Application Ser. No. 61/183,020 filed on Jun. 1, 2009. These applications are incorporated herein by reference in their entirety for all purposes.

FEDERALLY FUNDED RESEARCH

This invention was made with Government support under U01 AI070443 awarded by the National Institutes of Health. The Government has certain rights in this invention

FIELD

Embodiments of the present invention report compositions and methods for administering a vaccine to a subject against dengue viruses. In some embodiments, vaccine compositions may be administered by intradermal injection. In certain embodiments, intradermal injection in a subject of a vaccine against dengue virus may include one or more intradermal boosts after initial vaccination. Other embodiments include intradermal injection of a vaccine composition against dengue virus wherein the composition provides protection against more than one serotype of dengue virus, such as DEN-1, DEN-2, DEN-3 and DEN-4.

BACKGROUND

Vaccines for protection against viral infections have been effectively used to reduce the incidence of human disease. One of the most successful technologies for viral vaccines is to immunize animals or humans with a weakened or attenuated strain of the virus (a "live, attenuated virus"). Due to limited replication after immunization, the attenuated strain does not cause disease. However, the limited viral replication is sufficient to express the full repertoire of viral antigens and can generate potent and long-lasting immune responses to the virus. Thus, upon subsequent exposure to a pathogenic strain of the virus, the immunized individual is protected from disease. These live, attenuated viral vaccines are among the most successful vaccines used in public health.

SUMMARY

Embodiments of the present invention generally relate to methods and compositions for inducing protection in a subject against dengue virus by, for example, administering a vaccine to a subject against dengue viruses. Some embodiments can include introducing a vaccine composition to a subject via intradermal (ID) injection. In accordance with these embodiments, the vaccine composition can be introduced to a subject intradermally to, for example, protect against one or more than one dengue serotype (e.g. cross protection). In certain embodiments, a vaccine composition can include, but is not limited to, a single dose of one serotype of dengue virus (e.g. DENVax 4) administered to a subject. In other embodiments, a vaccine composition may include, but is not limited to; an initial dose of one serotype of dengue virus (e.g. DENVax 4 or other serotype) and then one or more boosts of the same, a combination or a different serotype can be administered to a subject.

Other aspects herein can concern inducing a cellular immune response in a subject by, for example, introducing a vaccine composition to a subject via intradermal introduction wherein the vaccine composition includes, but is not limited to, a dengue virus vaccine. In accordance with these embodiments, compositions disclosed can be administered intradermally to a subject for modulating neutralizing antibody production in the subject against dengue virus serotypes. Some aspects concern predetermined composition ratios (e.g. 1:1, 1:2, 1:4, any ratio of two or more serotypes is contemplated) of the various serotypes of dengue virus or fragments thereof or attenuated compositions thereof in a single vaccine composition in order to increase cross protection in a subject against some or all dengue virus serotypes when the subject is administered the single vaccine composition intradermally.

In certain embodiments, some advantages of using intradermal introduction of a vaccine against dengue virus can include, but are not limited to, multiple protection against some or all dengue virus serotypes in a subject, reduced cost by using small doses compared to subcutaneous injection, modulation of antibodies produced against some or all dengue virus serotypes in a subject and reduced pain at a site of administration in a subject administered a composition of vaccine against dengue virus.

In some embodiments, a single dose vaccine against dengue virus can include one or more dengue virus serotype(s). In accordance with these embodiments, a subject may be treated with at least one additional intradermal injection(s) administered at a separate site from the first injection, for example, next to or in a separate anatomical site on the subject. In addition, at least one additional intradermal injection(s) may be performed less than 30 days after the first administration to the subject. Vaccine compositions of these and other embodiments disclosed herein may include two or more dengue virus serotypes at a predetermined ratio.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

DEFINITIONS

As used herein, "a" or "an" may mean one or more than one of an item.

As used herein, vessel can include, but is not limited to, test tube, mini- or micro-fuge tube, channel, vial, microtiter plate or container.

As used herein the specification, "subject" or "subjects" may include but are not limited mammals such as humans or mammals, domesticated or wild, for example dogs, cats, other household pets (e.g., hamster, guinea pig, mouse, rat), ferrets, rabbits, pigs, horses, cattle, prairie dogs, or zoo animals.

As used herein, "about" can mean plus or minus ten percent.

As used herein, "attenuated virus" can mean a virus that demonstrates reduced or no clinical signs of disease when administered to a subject such as a mammal (e.g., human or an animal).

DESCRIPTION

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some cases, well-known methods or components have not been included in the description.

Certain aspects of the present invention include, but are not limited to, administration of vaccine compositions against dengue virus.

Embodiments of the present invention generally relate to methods and compositions for inducing protection in a subject against dengue virus serotypes. Other embodiments can include introducing a vaccine composition to a subject via intradermal (ID) injection wherein the vaccine composition introduced intradermally induces cross protection against some or all dengue serotypes. In certain embodiments, the vaccine composition comprises a single dose of a vaccine against dengue virus serotype 4 (DENVax 4) administered to a subject. In other embodiments, the vaccine composition comprises an initial dose of DENVax 4 then, one or more boosts of the vaccine administered to a subject.

Other aspects of the present invention include modulating an immune response to a vaccine against dengue virus administered intradermally compared to subcutaneously to a subject. Vaccines against dengue virus may include a composition comprising ratios of serotypes of dengue virus, live attenuated dengue virus, or fragments thereof such as proteins or nucleic acids derived or obtained from dengue virus serotypes. Ratios of various serotypes may be equal or certain serotypes may be represented more than others depending on need or exposure or potential exposure to the virus. In accordance with these embodiments, a ratio may be a 1:2, 1:3, 1:4, 1:10, 1:20; 1:1:1, 1:2:2, 1:2:1, 1:1:1:1, 1:2:1:2; 1:3:1:3, 2:3:3:3, 5:4:5:5, 1:2:2 or any ratio for any of serotypes 1, 2, 3 and/or 4, depending on for example, number of serotypes represented in the formulation, predetermined response and effect desired. It is contemplated that any dengue virus serotype formulation may be used to generate a vaccine (e.g. attenuated virus etc.) of use in intradermal administration to a subject in need thereof. It is contemplated that some formulations may be more effective than others when introduced intradermally than other formulations.

In other embodiments, compositions of dengue virus vaccine formulations may be introduced intradermally to a subject prior to, during or after exposure to dengue virus by the subject. In accordance with these embodiments, a subject may receive a single intradermal injection or more than one injection comprising a dengue virus formulation, optionally, followed by one or more additional injections. Intradermal applications of formulations described herein may be combined with any other anti-viral treatment or administration mode of vaccine (e.g. subcutaneous injection) to a subject. In some embodiments, it is contemplated that intradermal introduction of a formulation contemplated herein may be administered to any appropriate region of a subject's body (e.g. arm, hip, etc). In addition, intradermal administration of vaccine formulations herein as primary or boost administrations may occur in the same day, consecutive days, weekly, monthly, bi-monthly or other appropriate treatment regimen.

Methods

Nucleic Acid Amplification

Nucleic acids may be used in any formulation or used to generate any formulation contemplated herein. Nucleic acid sequences used as a template for amplification can be isolated viruses (e.g. dengue viruses), according to standard methodologies. A nucleic acid sequence may be genomic DNA or fractionated or whole cell RNA. Where RNA is used, it may be desired to convert the RNA to a complementary cDNA. In some embodiments, the RNA is whole cell RNA and is used directly as the template for amplification. Any method known in the art for amplifying nucleic acid molecules is contemplated (e.g., PCR, LCR, Qbeta Replicase, etc).

Expressed Proteins or Peptides

Genes can be expressed in any number of different recombinant DNA expression systems to generate large amounts of the polypeptide product, which can then be purified and used in methods and compositions reported herein. Any method known in the art for generating and using constructs is contemplated. In certain embodiments, genes or gene fragments encoding one or more polypeptide may be inserted into an expression vector by standard cloning or subcloning, techniques known in the art.

Proteins, peptides and/or antibodies or fragments thereof may be detected or analyzed by any means known in the art. In certain embodiments, methods for separating and analyzing molecules may be used such as gel electrophoresis or column chromatography methods.

Electrophoresis

Electrophoresis may be used to separate molecules (e.g., large molecules such as proteins or nucleic acids) based on their size and electrical charge. There are many variations of electrophoresis known in the art. A solution through which the molecules move may be free, usually in capillary tubes, or it may be embedded in a matrix or other material known in the art. Common matrices can include, but are not limited to, polyacrylamide gels, agarose gels, mass spec, blotting and filter paper.

Some embodiments, using a gene or gene fragment encoding a polypeptide may be inserted into an expression vector by standard subcloning techniques. An expression vector may be used which produces the recombinant polypeptide as a fusion protein, allowing rapid affinity purification of a peptide or protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.).

Pharmaceutical Formulations

Any pharmaceutical formulation known in the art for a vaccine is contemplated herein. In certain embodiments, a formulation can contain one or more DEN serotype in various ratios, depending on predetermined exposure to or existence of dengue virus subtypes. It is contemplated that formulations can contain other agents of use in vaccination of a subject including, but not limited to other active or inactive ingredients or compositions known to one skilled in the art.

Kits

Other embodiments concern kits of use with the methods (e.g. methods of application or administration of a vaccine) and compositions described herein. Some embodiments concern kits having vaccine compositions of use to prevent or treat subjects having, exposed or suspected of being exposed to one or more dengue viruses. In certain embodiments, a kit may contain one or more than one formulation of dengue virus serotype(s) (e.g. attenuated vaccines) at predetermined ratios. Kits can be portable, for example, able to be transported and used in remote areas such as military installations or remote villages. Other kits may be of use in a health facility to treat a subject having been exposed to one or more dengue viruses or suspected of being at risk of exposure to dengue virus.

Kits can also include a suitable container, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the agent, composition and any other reagent containers in close confinement for commercial sale. Such containers may include injection or blow-molded plastic containers into which the desired vials are retained. Optionally, one or more additional agents such as immunogenic agents or other anti-viral agents, anti-fungal or anti-bacterial agents may be needed for compositions described, for example, for compositions of use as a vaccine against one or more additional microorganisms.

The following examples are included to demonstrate certain embodiments presented herein. It should be appreciated by those of skill in the art that the techniques disclosed in the examples that follow represent techniques discovered to function well in the practices disclosed herein. However, those of skill in the art should, in light of the present disclosure, appreciate that many changes can be made in the certain embodiments which are disclosed and still obtain a like or similar result without departing from the spirit and scope herein.

EXAMPLES

Example 1

Previous studies revealed that natural infection with each DEN (dengue virus) serotype leads to long-lived protection against dengue fever caused by the homologous serotype. In certain embodiments, administration of an effective dengue vaccine closely mimics natural infection and can serve as a mode for administering vaccines against dengue virus. Embodiments reported herein can concern a natural infection route of dengue virus (DEN) infection, similar to intradermal delivery by the transporting host, a mosquito bite. In certain embodiments, intradermal injection to deposit the vaccine viruses into the same tissue can be used. Skin is a highly accessible organ and represents an effective immune barrier, mainly attributed to the presence of Langerhans cells (LCs) residing in the epidermis. Skin immunization elicits a broad range of immune responses, including humoral, cellular, and mucosal and has the potential to bypass the effect of pre-existing immunity on the immunogenicity of administered vaccines.

Figure 1:
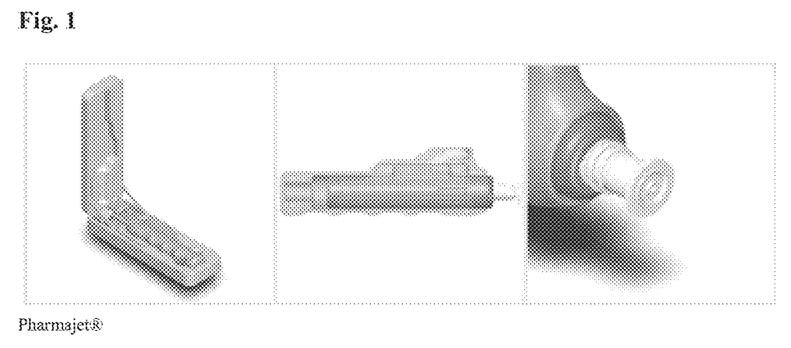
FIG. 1 represents an example of an intradermal injection device currently available.

Some embodiments for intradermal (ID) administration of the tetravalent dengue vaccines in a subject in need of such a treatment are reported. One exemplary method of intradermal administration was performed on four Cynomologous macaques administered a 5:5:5:5 DENVax (dengue virus vaccine) by intradermal administration. To achieve an equivalent dose of virus, 0.15 ml of vaccine was deposited ID in three closely spaced sites using a needle-free jet injector (see FIGS. 1 and 2, below). FIG. 1 represents an intradermal inject (e.g., PharmaJet®) device used for intradermal inoculations.

Figure 2:
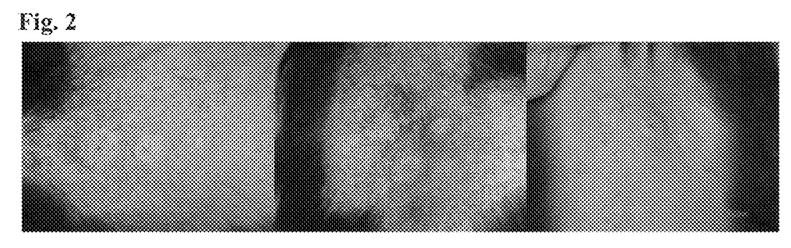
FIG. 2 represents examples of injection sites in a subject having intradermal introduction of a vaccine against dengue virus.

FIG. 2 illustrates inoculation sites on Cynomolgus macaques post vaccination with PharmaJet device. Animals were boosted 60 days later with the same formulation by the same route. Serum samples were collected at predetermined intervals, days 15, 30, 58, 74, and 91 and were tested for the presence of neutralizing antibodies directed against the four dengue serotypes. PRINT (plaque reduction neutralization test, known in the art for quantifying levels of anti-DEN neutralizing antibodies) were performed on the sera samples.

Figure 3:
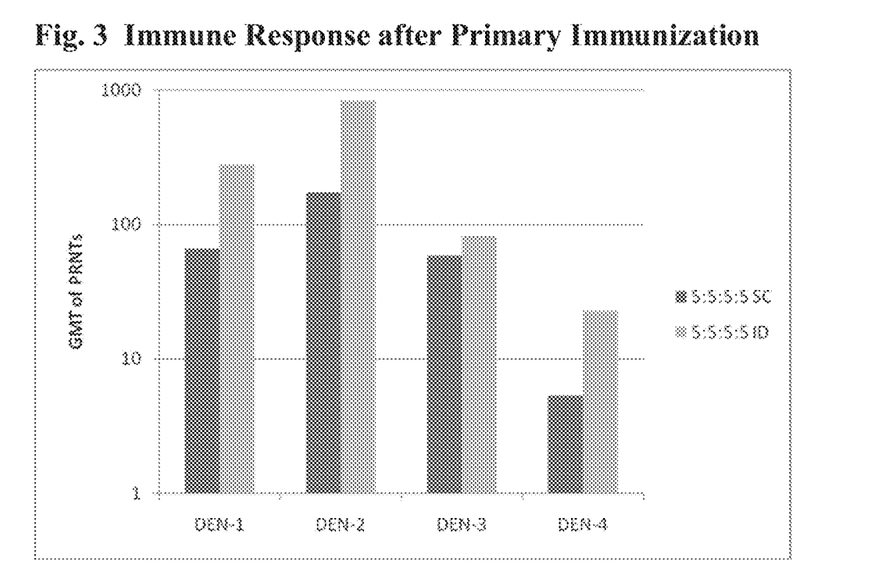
FIG. 3 represents a bar graph comparison of subcutaneous versus intradermal injection of a vaccine against dengue virus and neutralizing antibody titer produced against different dengue virus serotypes after a primary administration.
Figure 4:
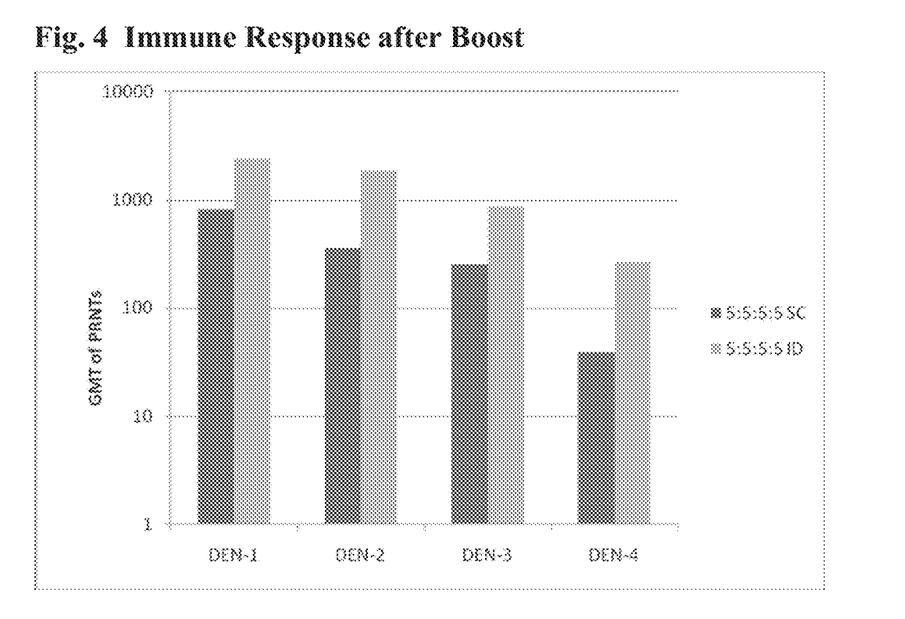
FIG. 4 represents a bar graph comparison of subcutaneous versus intradermal injection of a vaccine against dengue virus and neutralizing antibody titer produced against different dengue virus serotypes after a second, boosting administration.

It was demonstrated that the neutralizing antibody titers are significantly higher after ID administration as compared to SC administration after a primary administration (see FIG. 3) or after a secondary administration (See FIG. 4). Since the sites were closely spaced in the same, area, and each inoculum consists of all four viruses, this mode of vaccine delivery closely resembles a single administration of DENVax. FIG. 3 illustrates 50% PRNT Geometric Mean Titers at Day 58 (58 day's after the primary administration). FIG. 4 illustrates 50% PRNT Geometric Mean Titers at Day 74 (14 days after the secondary administration on Day 60). As can be seen in the figures, the neutralizing antibody titers to all four dengue viruses were higher after intradermal versus subcutaneous administration. In addition, the number of animals that demonstrated neutralizing antibody responses ("seroconversion" defined as PRNT>10) was greater after the first dose of vaccine (see Table 1, the percentage of animals that seroconverted to each of the four dengue serotypes is shown after primary and secondary immunization).

TABLE 1

Seroconversion of non-human primates after dengue immunization

| DENVax Formulation | DEN-1 Prime | DEN-1 Boost | DEN-2 Prime | DEN-2 Boost | DEN-3 Prime | DEN-3 Boost | DEN-4 Prime | DEN-4 Boost |
|---|---|---|---|---|---|---|---|---|
| 5:5:5:5 SC | 87.5% | 100.0% | 100.0% | 100.0% | 75.0% | 100.0% | 50.0% | 100.0% |
| 5:5:5:5 ID | 100.0% | 100.0% | 100.0% | 100.0% | 100.0% | 100.0% | 100.0% | 100.0% |

The immunized animals were tested for protection against challenge with wild type dengue viruses. In cynomolgus macaques, wild type dengue virus infection leads to virus replication and viremia, but no clinical signs. At day 91, two monkeys were challenged with DENV-1 (dengue virus serotype 1) and two monkeys challenged with DEN-2 (dengue virus serotype 2). Serum samples were collected daily for 11 days after challenge. Levels of dengue virus RNA were measured in the samples by quantitative real-time polymerase chain reaction technology (q-rtPCR) and titers of viable virus were measured by virus isolation and plaque formation on Vero cells. The results are shown in Tables 2 and 3. Neutralizing antibodies against DEN-1 at Day 91, just prior to challenge ("Pre-Challenge") and Day 105, 14 days after challenge ("Post"). Viremia is given as the number of days that live DEN-1 virus could be isolated from blood samples ("Duration") mid the log 10 of the peak titer isolated from each animal. Viral RNA is given as the number of days viral RNA could be detected in the serum samples ("Duration") and peak viral RNA levels in each monkey, expressed as the log 10 of the number of viral RNA genomes detected.

After challenge, the SC and immunized animals were completely protected from DEN-1 or DEN-2 induced viremia (compared to the control animals that demonstrated significant viremia of long duration). In all of the ID immunized animals, but not all of the SC immunized animals, there was also an absence of viral RNA replication and a lack of an increase in antibody titer after challenge (compare the ID animals to SC infected CY0181, CY0172 or the control animals). These data suggest that protection is "sterilizing" and prevents any virus replication after challenge.

Example 2

In another example, an optimized DENVax formulation delivered in different locations and with different timings will be tested in non-human primates. Groups of eight Cynomolgus macaques will be immunized with a DENVax formulation containing $1\times10^5$ plaque forming units (pfu), $1\times10^4$ pfu, $1\times10^5$ pfu and $1\times10^5$ pfu of DENVAx-1, DENvax-2, DENVax-3 and DENVax-4, respectively (abbreviated 5:4:5:5). Two doses will be administered in 0.1 ml ID.

TABLE 2

Responses after challenge with DEN-1

| Monkey | Formulation | DEN-1 PRNT Pre-Challenge | DEN-1 PRNT Post | Viremia Duration | Viremia Peak | Viral RNA Duration | Viral RNA Peak |
|---|---|---|---|---|---|---|---|
| CY0174 | 5:5:5:5 SC | 240 | 240 | 0 | 0 | 0 | 0 |
| CY0181 | 5:5:5:5 SC | 640 | 61440 | 0 | 0 | 5 | 5.6 |
| CY0192 | 5:5:5:5 ID | 1920 | 1280 | 0 | 0 | 0 | 0 |
| CY0194 | 5:5:5:5 ID | 7680 | 1920 | 0 | 0 | 0 | 0 |
| CY0061 | Controls | 1 | 2560 | 6 | 2.0 | 9 | 5.7 |
| CY0193 | Controls | 25 | 2580 | 3 | 2.7 | 7 | 6.4 |
| CY0058 | Controls | 1 | 640 | 5 | 2.9 | 7 | 5.5 |
| CY0073 | Controls | 1 | 1280 | 5 | 3.6 | 10 | 6.2 |

TABLE 3

Responses after challenge with DEN-2

| Monkey | Formulation | DEN-2 PRNT Pre-Challenge | DEN-2 PRNT Post | Viremia Duration | Viremia Peak | Viral RNA Duration | Viral RNA Peak |
|---|---|---|---|---|---|---|---|
| CY0172 | 5:5:5:5 SC | 3413 | 3413 | 0 | 0 | 1 | 3.9 |
| CY0177 | 5:5:5:5 SC | 853 | 533 | 0 | 0 | 0 | 0 |
| CY0198 | 5:5:5:5 ID | 240 | 320 | 0 | 0 | 0 | 0 |
| CY0201 | 5:5:5:5 ID | 1920 | 1600 | 0 | 0 | 0 | 0 |
| CY0088 | Controls | 6 | 10240 | 6 | 2.3 | 8 | 5.1 |
| CY0199 | Controls | 1 | 3840 | 5 | 1.8 | 9 | 4.7 |
| CY0065 | Controls | 1 | 10240 | 5 | 2.9 | 8 | 5.8 |
| CY0104 | Controls | 1 | 10240 | 4 | 2.4 | 8 | 5.7 |

Groups will be immunized with either one dose in each arm at Day 0, one dose in one arm at Day 0 and one dose in the other arm at Day 7, or one dose in one arm at Day 0 and one dose in the other arm at Day 60. These groups will be compared to a group that receives the same dose (5:4:5:5) in three sites in the same are on Day 0 and three sites in the other arm on Day 60 as well as a group that receives the same dose in a single 0.5 ml SC immunization in one arm at Day 0 and in the other arm at Day 60. A control group will be immunized with vaccine excipients only (no vaccine viruses). Following immunization blood samples will be collected on days 0, 7 (for peak viremia), 15, 30, 60, and 90 to test the neutralizing antibodies against the four dengue virus serotypes by PRNT50. PBMCs collected on days 30, 60, 90 will be also monitored for IFN-γ secretion by an ELISPOT assay. On day 90, two animals from each group will be challenged with wild type of DEN-1, DEN-2, DEN-3, or DEN-4 viruses. Challenged animals will be monitored for clinical signs and temperature (twice daily), changes in food consumption (once daily) and body weight (weekly). In addition, all animals will be bled daily for 11 days post-challenge to monitor viremia and hematological parameters. Again, the speed and duration of PRNT responses to all four DEN viruses and protection after day 90 challenge will be assessed. It is believed that intradermal administration in multiple sites and in distinct anatomical locations may be more effective than subcutaneous administration as a single bolus. Multiple sites can provide exposure of the vaccine to more antigen presenting cells. Distinct anatomical locations can permit vaccine access to multiple lymph nodes. In addition, booster immunizations of dengue vaccines have only been administered after the development of antibody responses in mice, primates and human clinical trials, thirty days or longer. At this time, neutralizing antibodies inhibit the response to the live viral vaccines. It was previously shown that boosting primates one month after primary immunization was less effective than dosing four months after primary immunization. It was speculated that high levels of homologous and heterologous antibodies that circulate after the initial immunization can inhibit viral replication in a second dose. While prolonged (two months or longer) immunization may circumvent this inhibition, it has not been tested whether accelerated immunization regimen with shorter immunization intervals, before the development of potent neutralizing antibody responses may be advantageous. Such a shortened regimen may be an advantage in endemic countries or for travelers, where exposure to dengue viruses in between the immunizations may put them at risk of disease.

Example 3

In another example, a human clinical trial has been initiated, studying the safety and immunogenicity of two DENVax formulations, administered in 0.1 ml either by ID or SC injection. Groups of 12 individuals will be immunized with for example, a low dose DENVax formulation ($8 \times 10^3$ pfu, $5 \times 10^3$ pfu, $1 \times 10^4$ pfu and $2 \times 10^5$ pfu of DENVax-1, -2, -3 and -4, respectively) or a high dose ($2 \times 10^4$ pfu, $5 \times 10^4$ pfu, $1 \times 10^5$ pfu and $3 \times 10^5$ pfu of DENVax-1, -2, -3 and -4, respectively) of DENVax ID or SC on Days 0 and 90. Two control groups will be injected SC or ID with phosphate-buffered saline. Patients will be monitored for any adverse events, and for any significant changes in hematological or blood chemistry parameters. Serum samples will be collected to measure vaccine virus replication and neutralizing antibody responses at periodic intervals.

Example 4

Immunogenicity and efficacy of DENVax administered intradermally in AG129 mice. In another example, two studies were performed to compare the effect of route of administration on immunogenicity and efficacy of DENVax AG129 mice. In one example, the immunogenicity of monovalent DENV$^a$x-4 (e.g. vaccine against one Dengue virus serotype) was compared in AG129 mice by measuring the neutralizing antibody responses following SC injection under the skin on the back or ID injection into the foot pad using a needle and syringe. Groups of 8 AG129 mice were injected ID or SC with $10^5$ PFU/dose of chimeric DENVax-4 vaccine in 50 µl and 100 µl final volume, respectively. Six weeks after priming, animals from each treatment group were boosted via the corresponding ID or SC route with $10^5$ PFU of DENVax-4 or TEA. Mice were bled on Day 31 and 58 and collected sera were pooled to measure neutralizing antibody responses.

Immunization of DENVax-4 via the ID route elicited a 5-fold higher neutralizing antibody response to DEN-4 after the boost compared to the response induced via the SC route (see for example, FIG. 4). The anti-DEN-4 response elicited by either route of immunization had a marked cross-neutralizing activity against DEN-3 but not against DEN-1 or DEN-2 serotypes. FIG. 4 represents neutralizing antibody responses following primary and secondary immunization of AG129 mice with chimeric DENVax-4. Mice were bled on Day 31 and 58 and collected sera were pooled to measure neutralizing antibody responses using the plaque reduction assay (PRNT50).

Figure 5:
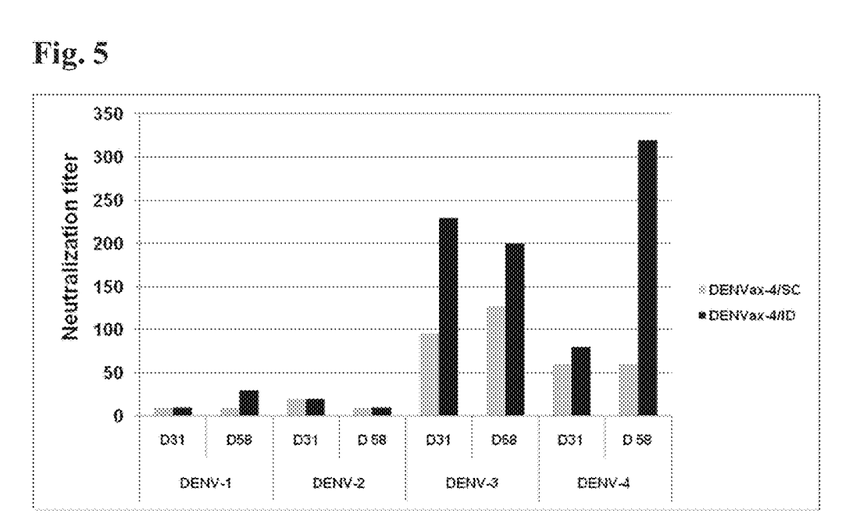
FIG. 5 represents a histogram plot of subcutaneous and intradermal immunizations with a vaccine against a dengue virus serotype in mice.
Figure 6A:
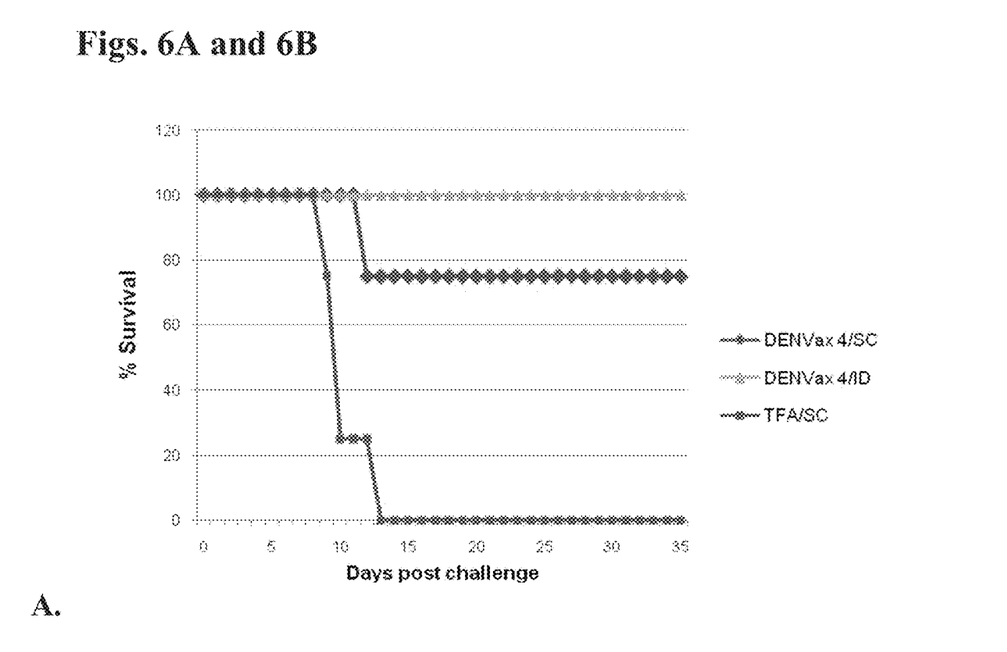
FIGS. 6A and 6B represent graphic depictions of a challenge experiment using two different dengue virus serotypes on a dengue serotype-immune mouse population following vaccination of the mice with another dengue virus serotype.
Figure 6B:
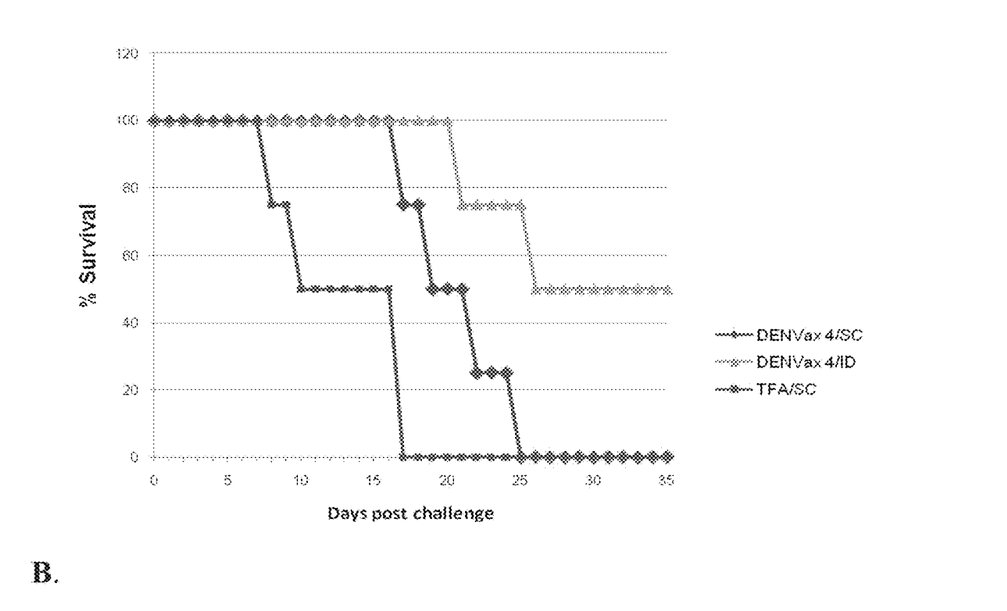

Two weeks after the boost animals from each group were split in to two groups and challenged with $10^6$ PFU of DEN-1 (Mochizuki virus strain) or DEN-2 (New Guinea C strain) viruses. Challenged animals were monitored for clinical signs of disease and survival rates were recorded over a period of 5 weeks. Mice immunized via the ID route showed no signs of disease after DEN-1 challenge (FIG. 5A). In the SC immunized group only one mouse succumbed to infection while the rest of animals had no any apparent signs of infection (FIG. 5B). In contrast, all control animals succumbed to infection by day 13 after DEN-1 challenge (FIG. 5A). Following DEN-2 challenge, all animals immunized with only DENVax-4 via the SC route succumbed to infection by day 25 with mean survival time (MST) of 19.5 days as compared to the control (TEA) mice that all succumbed by day 17 (MST=12.5 days) post-challenge (FIG. 5B). In contrast, fifty percent of ID DENVax-4 immunized mice survived the infection until the end of the 5 week monitoring period (FIG. 5B). FIGS. 5A and 5B represent survivals of DENVax-4 immune AG129 mice following challenge with DEN-1 (a) or DEN 2 (b) viruses. Challenged animals were monitored for clinical signs of disease and survival rates were recorded over a period of 5 weeks.

In a second study, immunogenicity of tetravalent DENVax vaccine administered SC or ID in mice (e.g. AG129) was tested. Groups of AG129 mice, six per group were injected SC or ID with the DENVax in 100 µl or 50 µl (final volume), respectively. Mice were immunized with DENVax at a 5:4:5:5 ($10^5$ PFU of DENVax-1, -3 and -4 and $10^4$ PFU of DENVax-2) dose level of composite chimeric vaccines. All immunized animals received a booster injection of 5:4:5:5 DENVax 42 days' post-primary inoculation. Blood samples were collected on days 42 and 56 to measure neutralizing antibody responses to each DEN virus serotype.

As represented in Table 4, both primary and secondary neutralizing antibody responses to all four DEN serotypes were induced. Following the boost, the neutralizing anti-DEN-1, DEN-3 and DEN-4 antibody titers were increased by 2, 5 and 2 fold, respectively in the group of mice injected ID as compared to the SC immunized animals. Neutralizing responses to DEN-2 virus were comparable in both groups. Immunization via the SC route resulted in a profile of dominant neutralizing antibody responses against DEN-1>DEN-2>DEN-3>DEN-4, with neutralizing titers 5120, 1280, 640 and 80, respectively. The hierarchy of neutralizing antibody responses after ID administration had shifted as follows; DEN-1>DEN-3>DEN-2>DEN-4 with neutralizing antibody titers 10240, 3840, 1280 and 160, respectively.

TABLE 4

Comparison of the immunogenicity of tetravalent DENVax bearing the ratio 5:4:5:5 PFU of each composite chimeric virus ($10^5$ PFU of DENVax-1, -3 and -4 and $10^4$ PFU of DENVax-2) after SC or ID immunization of mice. Blood samples were collected on days 42 and 56 to measure neutralizing antibody responses to each DEN virus serotype.

| DENVax Formulation | Neutralizing Antibody Titers (GMT) | | | | | | | |
|---|---|---|---|---|---|---|---|---|
| | DEN-1 | | DEN-2 | | DEN-3 | | DEN-4 | |
| | Prime | Boost | Prime | Boost | Prime | Boost | Prime | Boost |
| 5:4:5:5/SC | 1920 | 5120 | 3200 | 1280 | 1280 | 640 | 80 | 80 |
| 5:4:5:5/ID | 2560 | 10240 | 1280 | 1280 | 1600 | 3840 | 120 | 160 |

Materials and Methods

Mice: AG129 mice have an "intact" immune system; deficient for the interferon (IFN)-α/β and -γ receptors. Dengue infection has been described. Other studies: pathogenesis, cell tropism, and ADE have been examined. This model permits challenge with DEN-1 and DEN-2.

Non-human primates: Cynomolgus, rhesus macaques carry virus (viremia), but no disease manifests.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations may be applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A method for inducing an immune response in a subject against all four dengue virus serotypes, comprising, administering to the subject by at least a first introduction, an immunogenic composition of a mixture comprising components of all four dengue virus serotypes, the composition comprising at least one live, attenuated dengue chimera comprising dengue-2/1, dengue-2/3 and dengue-2/4; and at least a non-chimera live, attenuated dengue-2 virus, and administering at least a second introduction of the immunogenic composition within 30 days of but not on the same day as, the first introduction to the subject and inducing an immune response in the subject against all four dengue virus serotypes.

2. The method of claim 1, wherein administering the at least a second introduction occurs at a separate anatomical site on the subject as the first introduction.

3. The method of claim 1, wherein the all four dengue virus serotypes are represented at a predetermined ratio in the immunogenic composition.

4. The method of claim 1, further comprising administering at least one additional immunogenic agent against dengue virus to the subject as part of or separately from, the first immunogenic composition.

5. The method of claim 4, wherein the additional immunogenic agent comprises at least one Toll receptor (TLR) ligand(s) and the additional immunogenic agent is added to the first immunogenic composition prior to administration to the subject.

6. The method of claim 1, wherein the mixture of the four dengue virus serotypes comprises a live, attenuated dengue-2 virus, and at least one live, attenuated dengue chimera wherein capsid and non-structural proteins are from the live, attenuated dengue-2 virus, and wherein the backbone of the dengue chimera is dengue-2; and pre-membrane and envelope proteins are from at least a second, different dengue virus serotype.

7. The method of claim 6, wherein the pre-membrane and envelope proteins of the at least a second dengue virus are from dengue-1, dengue-3 or dengue-4.

8. The method of claim 6, wherein the at least one live, attenuated dengue chimeras are two or more of dengue-2/dengue-1, dengue-2/dengue-3 and dengue-2/dengue-4.

9. The method of claim 6, wherein the live, attenuated dengue-2 virus concentration is reduced compared to the at least one dengue chimera in the immunogenic composition.

10. A method for inducing an immune response in a subject against dengue virus serotypes, comprising, administering to the subject by a first introduction, a first immunogenic composition of four live, attenuated dengue viruses wherein the first immunogenic composition comprises live, attenuated dengue-2 virus wherein the live, attenuated dengue-2 virus is not chimeric; and three dengue chimeras of live, attenuated dengue viruses of dengue-2/1, dengue-2/3 and dengue-2/4; administering a second introduction of the first immunogenic composition within 30 days of but not on the same day of administration of the first introduction and inducing an immune response in the subject against all four dengue virus serotypes.

11. The method of claim 10, administering at least a second immunogenic composition in the same anatomical area as the first introduction.

12. The method of claim 10, administering at least a second immunogenic composition at a separate anatomical area on the subject from the first introduction.

13. The method of claim 10, wherein the four dengue virus serotypes of the first immunogenic composition comprise a predetermined ratio of one dengue virus serotype to another dengue virus serotype in the first immunogenic composition.

14. The method of claim 13, wherein the live, attenuated dengue-2 virus concentration is reduced compared to the at least one dengue chimera in the immunogenic composition.

15. The method of claim 1, wherein the immunogenic composition is administered to the subject by intradermal or subcutaneous administration.

\* \* \* \* \*